United States Patent
Jansen et al.

(10) Patent No.: US 7,214,719 B2
(45) Date of Patent: May 8, 2007

(54) CHEMICAL REACTION AND SEPARATION METHOD

(75) Inventors: Jacobus Cornelis Jansen, Delft (NL); Frederik Kapteijn, Purmerend (NL); Sander Adriaan Strous, Schiedam (NL)

(73) Assignee: Technische Universiteit Delft, Delft (NL)

( * ) Notice: Subject to any disclaimer, the term of this patent is extended or adjusted under 35 U.S.C. 154(b) by 247 days.

(21) Appl. No.: 10/965,660

(22) Filed: Oct. 15, 2004

(65) Prior Publication Data
US 2005/0184009 A1 Aug. 25, 2005

(30) Foreign Application Priority Data
Oct. 17, 2003 (EP) ................... 03078287

(51) Int. Cl.
C07C 27/00 (2006.01)
B01D 15/00 (2006.01)

(52) U.S. Cl. ...................... 518/700; 210/640
(58) Field of Classification Search ............... 518/700; 210/640
See application file for complete search history.

(56) References Cited

U.S. PATENT DOCUMENTS

| 5,419,884 A | 5/1995 | Weekman et al. |
| 6,379,436 B1 | 4/2002 | Kuznicki et al. |
| 6,403,660 B1 | 6/2002 | Espinoza et al. |

OTHER PUBLICATIONS van den Berg et al., "Zeolite A Membranes Synthesized on a UV-Irradiated $TIO_2$ Coated Metal Support: The High Pervaporation Performance," Journal of Membrane Science, 224, pp. 29-37 (2003).

Kazemimoghadam et al., "Dehydration of Water/1-1-Dimethylhydrazine Mixtures By Zeolite Membranes," Microporous and Mesoporous Materials, 70, pp. 127-134 (2004).

Cha et al., "Removal of Water Vapor and VOCs From Nitrogen In a Hydrophilic Hollow Fiber Gel Membrane Permeator," Journal of Membrane Science, 119, pp. 139-153 (1996).

Primary Examiner—J. Parsa
(74) Attorney, Agent, or Firm—Fitch, Even, Tabin & Flannery

(57) ABSTRACT

The invention is directed to process for performing a chemical reaction in a reaction mixture, which reaction produces water as by-product, wherein the reaction mixture is in contact with a hydroxy sodalite membrane, through which water produced during the reaction is removed from the reaction mixture, to a process for removing water form mixtures thereof.

14 Claims, 3 Drawing Sheets

Figure 2:
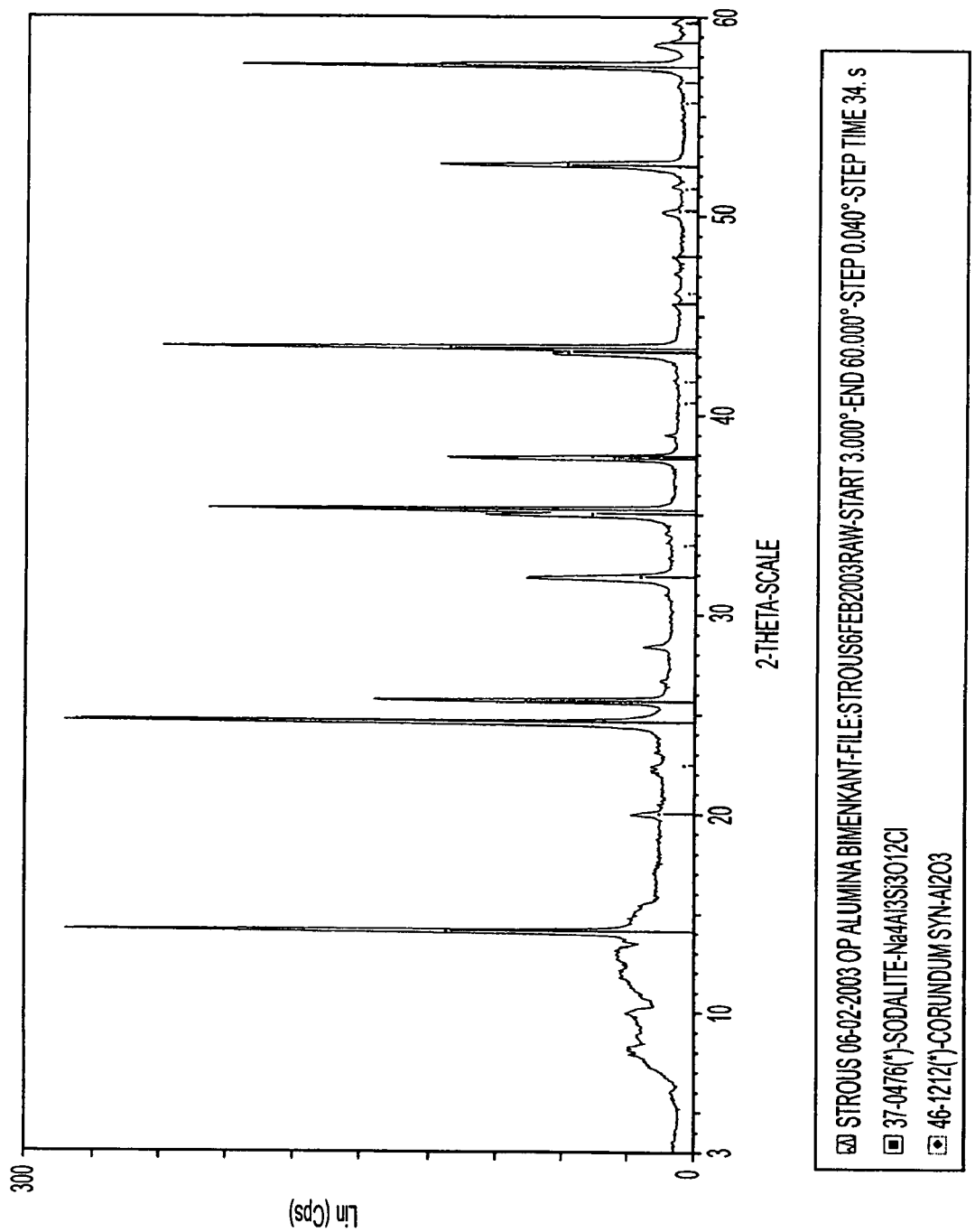
Figure 3A:
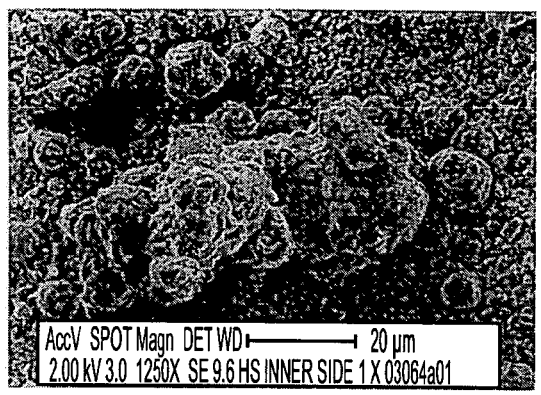
Figure 3B:
Figure 3C:
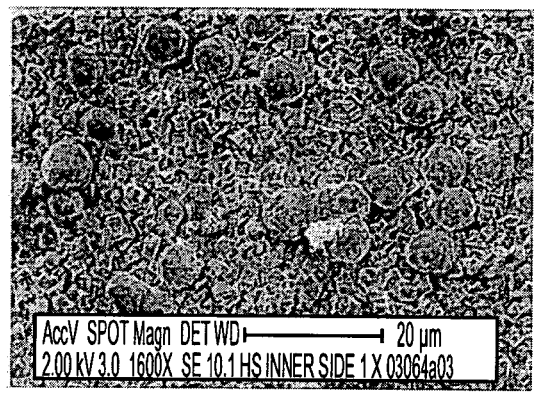
Figure 3D:
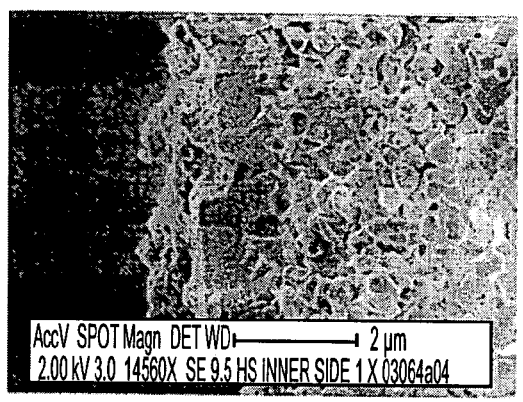

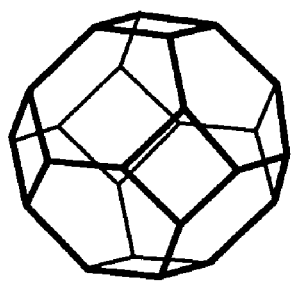
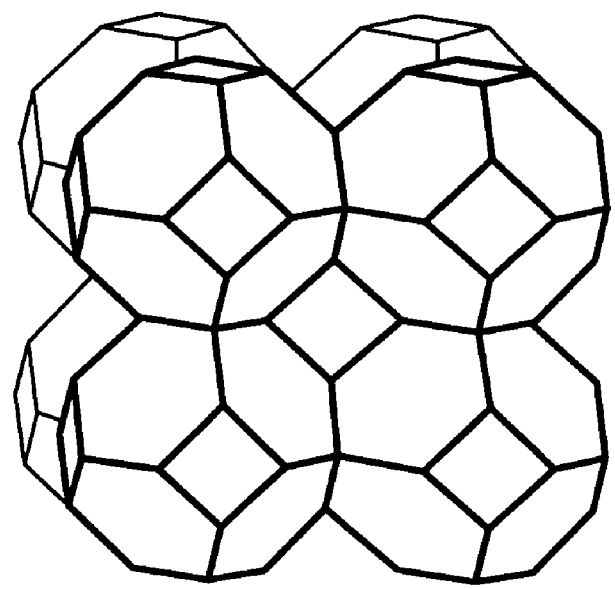
FIG. 1A                    FIG. 1B

CHEMICAL REACTION AND SEPARATION METHOD

This U.S. application claims the foreign priority benefit, under 35 U.S.C. §119, from EP 03078287.4, filed Oct. 17, 2003, the complete disclosure of which is incorporated herein by reference.

BACKGROUND OF THE INVENTION

The present invention is directed to a process for performing a chemical reaction, to a process for separating water from a mixture containing water, to a membrane suitable for such processes and to a process for preparing a membrane.

Modern chemical engineering has a focus on the integration of reaction and separation. In-situ separation of water from the Fischer-Tropsch reaction mixture is an example of such integration. The continuous removal of water, which is produced as a side product, contributes to an improvement of conversion, product selectivity and catalyst life time.

More in general it can be remarked, that the removal of water from mixtures with water is a very important aspects in various areas of chemical engineering and process technology. In reactions where water is a by-product, be it an equilibrium reaction or a non-equilibrium reaction, the continuous removal of water produced, from the reaction mixture helps to improve the reaction efficiency.

Separating of water from mixtures thereof, more in particular with $H_2$, CO, $CO_2$, $CH_4$ and higher alkanes, is also very important, more in particular in case the other component(s) need(s) to be dry, for example for further reaction or use.

Separation can be based on several principles. With a hydrophilic membrane, it is possible to separate water from for example a mixture of water and an organic component. The separation principle is based on the preference of the membrane for adsorbing water. Also separation on size is possible, when the components to be separated are small enough in kinetic diameter to migrate through the zeolite pores and the components from which they have to be separated have a kinetic diameter that is too large.

The kinetic diameter can be understood as the diameter of a pore needed to let that specific molecule pass. Water has a kinetic diameter of 2.65 Å, even smaller than that of hydrogen. Thus separation based on geometry is possible, when one finds a zeolite with a pore size large enough to enable water to pass and to exclude hydrogen and other larger molecules. It was generally assumed that 6-membered rings were unsuitable for this type of separation.

In most chemical reactions with water as by-product, water has the smallest kinetic diameter. For example in a Fischer-Tropsch reaction mixture the kinetic diameters of $H_2$, CO and linear alkanes are respectively 2.89, 3.76 and 4.3 Å.

SUMMARY OF THE INVENTION

The invention is based on the surprising discovery that it is possible to continuously separate water from reaction mixtures, more in particular Fischer-Tropsch reaction mixtures, by the use of a hydroxy sodalite membrane.

Sodalite is a zeolite having as the largest apertures exclusively 6-membered rings, so-called sodalite cages. Hydroxy sodalite (sodalite hydrate, hydroxo sodalite) is the hydrated form of sodalite. It can be synthesized without a template from an aqueous solution and then contains water molecules in all its pores. The hydroxy sodalite is used without activation.

A definition of hydroxy sodalite can be found in "Atlas of Zeolite Frameworks, 5$^{th}$ revised Ed. Elsevier 2001, pages 254 and 255. In FIG. 1, the structure has been given.

Hydroxy sodalite belongs to the group of feldspathoids and is a so-called cubic feldspathoid. It is entirely built of the so-called β-cages. These cages are truncated octahedrons (left structure of FIG. 1). A truncated octahedron has 6 square faces and 8 hexagonal faces, which give it 36 edges and 24 vertices. A T (tetrahedral) atom (Si, Al) is located at each vertex. Oxygen atoms are located between the tetrahedral atoms (but not necessarily on the edge). So the edges are not meant to portray bonds, but merely the geometry of the polyhedron. In sodalite, this polyhedral arrangement can be distorted so that the exact arrangement of oxygen atoms is not regular.

In a first embodiment the invention is directed to a process for performing a chemical reaction in a reaction mixture, which reaction produces water as by-product, wherein the reaction mixture is in contact with a hydroxy sodalite membrane, through which water produced during the reaction is removed from the reaction mixture.

A second embodiment is directed to a process for separating water from a mixture thereof with at least compound from the group of $H_2$, CO, $CO_2$, $CH_4$ and higher alkanes, said process comprising passing the mixture over a hydroxy sodalite membrane and removing the water throughthe membrane.

A third embodiment concerns an especially suitable membarne or use in these processes, namely a tubular hydroxy sodalite membrane supported on a tubular porous ceramic support.

A 4$^{th}$ and final embodiment of the invention concerns a process for preparing a supported hydroxy sodalite membrane said process comprising providing a suitable porous membrane support material, preferably a ceramic support material, providing a solution of a silicate and an aluminate in water and reacting the solution under hydrothermal conditions to produce a hydroxy sodalite layer on the surface of the porous material.

DETAILED EMBODIMENTS

As indicated above, in a first embodiment, the invention resides therein that water is removed continuously from the reaction mixture of a reaction wherein water is a by-product. By passing the reaction mixture along the surface of a hydroxy sodalite membrane, the water is removed from the reaction mixture. Preferably the temperature is at least 100° C. Above this temperature the structure of the sodalite is slightly distorted thereby easing the transfer of water through the membrane, which would otherwise be very difficult, as the diameter of the 6-membered cages is slightly smaller than the kinetic diameter of water. Preferably the temperature is between 150° C. and 500° C. Above these temperatures the stability of the hydroxy sodalite decreases.

Generally, there are two separation methods with membranes: pervaporation and gas or vapour permeation. Pervaporation is the separation through a membrane with on the feed side a liquid mixture and an applied vacuum or lower pressure on the permeate side which makes the permeated components evaporate. With gas permeation both the feed mixture at the feed side and the separated components on the permeate side are in gas phase.

It may be advantageous to use increased pressure, as this increases the partial pressure of the reaction mixture, in case the water is present in the gaseous phase. Suitable pressures are between 0.5 bar (abs) to 100 bar (abs).

The membrane is preferably supported on a suitable porous support, such as a metal or, most preferred, a ceramic support, such as sintered α-alumina. Optionally, a mesoporous layer, such as a silica or titania layer, may be present between the support and the hydroxy sodalite layer. The thickness of the membrane is preferably between 1 and 50 μm, more preferred between 5 and 20 μm.

The membrane has to have a closed structure, i.e. there should be substantially no cracks or holes in the membrane, other than the pores of the sodalite structure.

In order to improve the flux, it is possible to flush the permeate side of the membrane with a dry gas.

Suitable reactions in the context of the present invention are the Fischer-Tropsch synthesis, condensation reactions and dehydration reactions.

Besides the well-known conventional production of fuels from oil, that is called refining, there is a 'gas to liquids' process (named the Fischer-Tropsch process). In this process carbon monoxide and hydrogen, together called the synthesis gas, are converted over an iron or cobalt catalyst (in fact it is the catalytic hydrogenation of carbon monoxide) into a mixture of hydrocarbons and water [1,2]. The basic general reaction is as follows:

$$nCO+(2n+1)H_2 \rightarrow C_nH_{2n+2}+nH_2O$$

The hydrocarbons are synthesized by a chain growth process, with the length of the chain dependent on the catalyst selectivity and reaction conditions. The products formed primarily are normal paraffins, but α-olefins and alcohols are formed as well.

Suitable reaction conditions for FT reactions comprises pressures of between 5 and 50 bar(abs) and temperatures between 150° C. and 500° C., temperatures of about 250° C. (low temperature reaction) or 450° C. (high temperature) being preferred.

Water that is formed can react with carbon monoxide to form hydrogen and carbon dioxide in the so-called water-gas-shift reaction, an unwanted side reaction:

$$CO+H_2O \leftrightharpoons CO_2+H_2$$

In the early Fischer-Tropsch (FT) process methane reacts with air over a catalyst to create the synthesis gas, but this syngas can also be obtained from coal or even biomass gasification. Next to the main advantage of the Fischer-Tropsch process, which is the independence from oil, there is the advantage of making a cleaner product that, for example, contains no sulphur or aromatics.

Removal of water accordingly is advantageous for the reaction, not only because the subsequent reaction of CO and water is suppressed and the volume of the reactor is used more efficiently, but also because no ageing of the catalyst occurs. In general the same arguments apply to the other reactions, such as condensation reactions (which are generally equilibrium reactions, so that automatically the removal of water drives the reaction in the right direction) and dehydration reaction, for example the dehydration of hydroxy-group containing hydrocarbons to unsaturated hydrocarbons, more in particular alkanol to alkene.

For the second embodiment, the separation of water from various mixtures with other compounds, generally the same considerations apply with respect to the temperature, pressure and membrane structure.

More in particular the invention is suitable for drying methane and higher alkanes ($C_2$–$C_{10}$), and removing water from $H_2$, CO and $CO_2$.

The invention is further directed to the membrane itself and the process of making it. The membrane itself has already been described in relation to the other two embodiments.

The process for preparing a suitable membrane, comprises providing a suitable porous membrane support material, preferably a ceramic support material, such as α-alumina, steel coated with titania and the like providing a solution of a silicate and an aluminate in water and reacting the solution under hydrothermal conditions to produce a hydroxy sodalite layer on the surface of the porous material. Hydrothermal conditions are preferably temperature of at least 125° (up to 500° C.),for a period of at least 2 hours, preferably under autogenous conditions. Once the required sodalie material has been formed, the reaction is stopped and the hydroxy sodalite is washed. The membrane is then ready for use, as no activation is needed. Actually, the conventional activation procedure to burn away a template is detrimental to the material.

The supported membrane modules may subsequently be fitted into a membrane cell, with one or more tubular modules, in which the ends of the tubes are fitted with sealing means to make sure that the inside and outside of the membranes are only connected through the pores of the membrane. This gas-tight membrane sealing is thus very important for a good functioning of the membrane. For the best results epoxy-resin sealing or graphite ring sealing are preferred, since. (fluorelastomere) rubber rings failed.

The membranes of the invention have a flux which may be at least 1 kg of water/m²/h, even up to 2 kg/m²/h or higher. Based on these values the skilled person can easily calculate the membrane surface area required for a given reaction or separation. For example for a commercial FT reactor at industrial scale producing 1250 ton/day, a membrane surface of about 10,000 m² would suffice.

EXAMPLES

Preparation of a Membrane

α-alumina tubes having the following dimensions: 21 mm outer diameter, 18 mm inner diameter, 58 mm in length and a wall thickness of 1.5 mm were prepared. The pore size distribution is symmetrical (radially) with average pore size 0.07–0.1 microns. The whole tube consists of α-alumina there is no γ-alumina present (Steenkamp, Ph. D. thesis, University Twente)

The tubes have been sintered from Sumitomo AKP alumina powders at 1050° C. for 60 minutes, with a heating/cooling rate from and to room temperature of 1° C./min.

Prior to synthesis, the tubes need to be cleaned, in order to remove dust and other impurities. After the support was manufactured cleaning with an ammonium hydroxide and hydrogen peroxide solutions mixture was carried out.

Just before the synthesis the supports were washed with ethanol solutions, and finally with water. The latter two washings were done in sonificated baths. The outer side of the tubes was covered with a teflon tape (the one used for example to make tap water lines leak-proof). Ultimately runs have been performed with epoxy-resin sealing on Teflon holders. syntheses in rotating autoclaves seemed (according to SEM analysis) to give a better zeolite layer on the support. One explanation could be the removal of little air bubbles on the surface of the support by the continuous rotation. Defects in the zeolite layer can be accredited to these bubbles. The second modification was a change in nutrient concentration. SEM-pictures showed large agglomerates of crystals (so called 'cauliflowers') freely formed as well as attached to the support and zeolite layer. These agglomerates indicate a too large amount of nutrients, which induces unwanted free crystal growth next to the (wanted) zeolite crystal growth on the support. Several syntheses with decreased amounts of Si and Al (but always with a high pH) lead to a final modified synthesis mixture composition (table 1)

TABLE 1

Final modified synthesis mixture

|  | weight [g] | Mw [g mol$^{-1}$] | mol | molar ratio |
|---|---|---|---|---|
| Sodium hydroxide | 3.495 | 40 | 0.087375 | 16 |
| Sodium aluminate | 0.223 | 84 | 0.002654 | 0.5 |
| Sodium metasilicate | 1.134 | 212 | 0.005349 | 1 |
| Water | 47.064 | 18 | 2.615 | 489 |

Prior to the syntheses two mixtures were made in two separate polyethylene flasks. One (mixture A, table 2) contained the silica source, in this case sodium metasilicate dissolved in water with a high pH (so with a part of the sodium hydroxide). The other mixture (mixture B, table 3) also contained NaOH in water, and with the aluminium source, sodium aluminate. Both mixtures were well stirred for half an hour (in order to dissolve and hydrolyse the oxides) at ambient temperature.

TABLE 2

Composition mixture A

| Components mixture A | weight [g] |
|---|---|
| Sodium metasilicate | 1.134 |
| Sodium hydroxide | 1.483 |
| Water | 23.532 |

TABLE 3

Composition mixture B

| Components mixture B | weight [g] |
|---|---|
| Sodium aluminate | 0.223 |
| Sodium hydroxide | 2.012 |
| Water | 23.532 |

Subsequently the two mixtures were poured together and stirred well for another half hour (in order to obtain complete mixing of the components. In order to prevent pre-crystallisation half an hour aging was applied when preparing synthesis mixtures for zeolite growth on supports.

After this the mixture was put in a stainless steel autoclave with a teflon inner liner and the support (whether stainless steel with an TiO$_2$ layer or α-alumina). The autoclave was put in an oven (on a rotating axis in case of the rotating synthesis) for 3 hours at 140° C. Afterwards the autoclave was well cooled with tap water. Not only to stop the crystallisation (if the reaction continues zeolite A will be formed), but also for safety reasons: the caustic solution inside the autoclave is at its autogenic pressure. Subsequently the zeolites were filtered from the mixture and washed with water. In case of on-support growth, the 'coated' support is cleaned thoroughly with water.

XRD provided clarification that sodalite was made and whether other crystalline phases were present (zeolite A, quartz). For powders a Philips PW 1840 was used. Supported zeolite layers were identified by the Philips XRD of the Department of Materials Science of DelftChemTech (DCT), where also some sodalite powders have been analysed. FIG. 2.

SEM pictures were taken on a Philips XL20 SEM at the Polymers Department (PME) of Delft Technical University and at a Philips SEM with EDAX elemental analysis at the TNO Prins Maurits Laboratories (PML) in Rijswijk. FIG. 3.

Water/Octane separation

Tests were carried out at temperatures around 160° C. and low pressures. The pressure should be high enough to have a certain pressure drop over the membrane. A pressure drop of 2 bar was chosen and with the permeate side at atmospheric pressure, a total absolute pressure of 3 bar at the feed side was used. To ensure that the mixture was in the vapour phase, temperatures were chosen well enough above the boiling temperatures of octane and water at 3 bara. A working temperature was chosen well above the boiling point of least volatile component (i.e. octane) at the specific pressure applied.

The resulting permeate was obtained and analysed. No Octane was found therein, only water.

The invention claimed is:

1. A process for performing a chemical reaction in a reaction mixture, which reaction produces water as by-product, wherein the reaction mixture is in contact with a hydroxy sodalite membrane, through which water produced during the reaction is removed from the reaction mixture.

2. The process according to claim 1, wherein the said hydroxy sodalite membrane is supported on a porous support.

3. The process according to claim 2, wherein the support is an α-alumina support.

4. The process according to any one of claims 1–3, wherein the removal of water through the membrane occurs at (i) elevated temperature, (ii) a temperature of at least 100° C., or (iii) a temperature between 150° C. and 500° C.

5. The process according to claim 1, wherein the said chemical reaction is a Fischer-Tropsch reaction, a condensation reaction or a dehydration reaction.

6. The process according to claim 5, wherein the said reaction comprises a Fischer-Tropsch synthesis or the production of alkene from alkanol.

7. The Process according to claim 1, wherein the reaction is a slurry phase reaction and the reaction mixture is continuously passed along the surface of the membrane, the membrane being a tubular supported membrane.

8. The process for separating water from a mixture thereof with at least one compound selected from the group consisting of $H_2$, CO, $CO_2$, $CH_4$ and higher alkanes, said process comprising passing the mixture over a hydroxy sodalite membrane and removing the water through the membrane.

9. The process according to claim 8, wherein said hydroxy sodalite membrane is supported on a porous support.

10. The process according to claim 9, wherein the support is an α-alumina support.

11. The process according to any one of claims 8–10, wherein the removal of water through the membrane occurs at (i) elevated temperature, (ii) a temperature of at least 100° C., or (iii) a temperature between 150° C. and 500° C.

12. The process according to claim 8, wherein the said membrane is a tubular membrane.

13. The process according to claim 2, wherein said hydroxy sodalite membrane is supported on a ceramic support.

14. The process according to claim 9, wherein said hydroxy sodalite membrane is supported on a ceramic support.

* * * * *